(12) United States Patent
Weber et al.

(10) Patent No.: US 9,579,455 B2
(45) Date of Patent: Feb. 28, 2017

(54) CONTINUOUS INFUSION DEVICE

(71) Applicant: H & B ELECTRONIC GMBH & CO. KG, Deckenpfronn (DE)

(72) Inventors: Wilfried Weber, Schopfloch (DE); Tobias Morlok, Mötzingen (DE)

(73) Assignee: H & B ELECTRONIC GMBH & CO. KG, Deckenpfronn (DE)

( * ) Notice: Subject to any disclaimer, the term of this patent is extended or adjusted under 35 U.S.C. 154(b) by 151 days.

(21) Appl. No.: 14/417,033

(22) PCT Filed: Dec. 18, 2013

(86) PCT No.: PCT/EP2013/003825
§ 371 (c)(1),
(2) Date: Jan. 23, 2015

(87) PCT Pub. No.: WO2014/111114
PCT Pub. Date: Jul. 24, 2014

(65) Prior Publication Data
US 2015/0265764 A1 Sep. 24, 2015

(30) Foreign Application Priority Data

Jan. 16, 2013 (DE) .................... 20 2013 000 411 U

(51) Int. Cl.
*A61M 5/00* (2006.01)
*A61M 5/168* (2006.01)
(Continued)

(52) U.S. Cl.
CPC ...... *A61M 5/16877* (2013.01); *A61M 5/1413* (2013.01); *A61M 5/1454* (2013.01);
(Continued)

(58) Field of Classification Search
CPC .............. A61M 5/1456; A61M 5/1454; A61M 2005/14506; A61M 5/1452; A61M 5/14566; A61M 5/16877; Y10S 128/01
See application file for complete search history.

(56) References Cited

U.S. PATENT DOCUMENTS 1,983,276 A * 12/1934 Ehrenhaft .............. G03B 31/02
226/190
2,255,868 A * 9/1941 Wise .................... H04N 1/0057
358/469

(Continued)

FOREIGN PATENT DOCUMENTS

DE 29 06 830 B1 8/1980
DE 100 04 496 A1 8/2000
(Continued)

*Primary Examiner* — Kevin C Sirmons
*Assistant Examiner* — William Carpenter
(74) *Attorney, Agent, or Firm* — Birch, Stewart, Kolasch & Birch, LLP

(57) ABSTRACT

A continuous infusion device with a housing, in which an infusion device can be inserted. The infusion device includes at least one infusion liquid container which can be pressed out; an actuating device for pressing out the infusion device; a drive for moving the actuating device, the drive having a mechanical energy storage device; and a mechanical control arrangement, wherein a speed of the actuating device can be adjusted. The control arrangement has a brake device that provides at least one brake element, which can be braked and is motion-coupled to the drive, and a magnetic member wherein a magnetic field can be generated that applies a brake force to the brake element.

18 Claims, 3 Drawing Sheets

Figure 1:
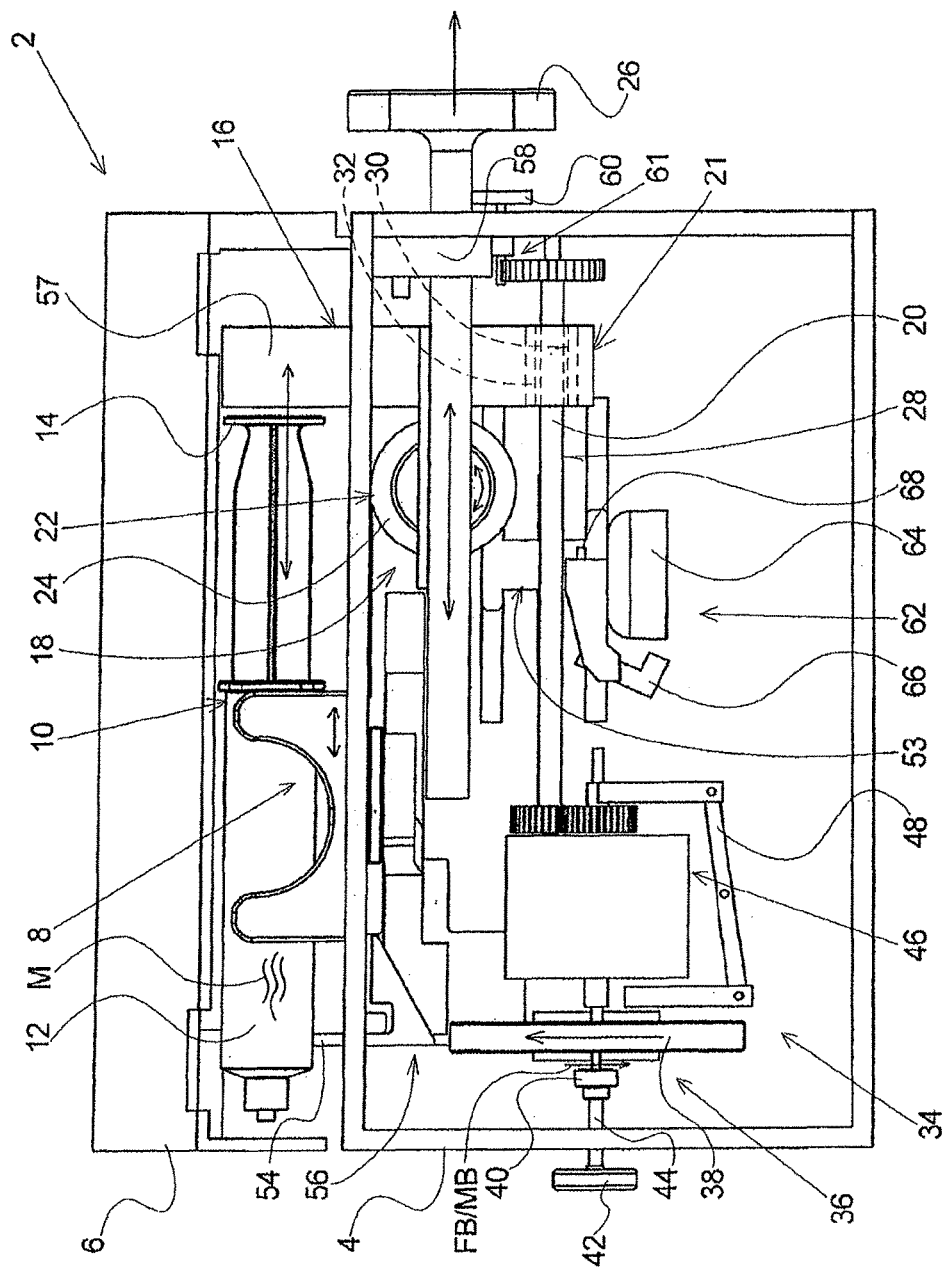

(51) Int. Cl.
*A61M 5/145* (2006.01)
*A61M 5/14* (2006.01)
*A61M 5/50* (2006.01)

(52) U.S. Cl.
CPC ........ *A61M 5/1456* (2013.01); *A61M 5/5086* (2013.01); *A61M 2205/0272* (2013.01); *A61M 2205/10* (2013.01); *A61M 2205/18* (2013.01); *A61M 2205/3317* (2013.01); *Y10S 128/01* (2013.01)

(56) References Cited

U.S. PATENT DOCUMENTS

| | | | | |
|---|---|---|---|---|
| 2,602,446 | A * | 7/1952 | Glass | A61M 5/1452 |
| | | | | 128/DIG. 1 |
| 3,785,923 | A * | 1/1974 | Bratoljic | G21C 7/14 |
| | | | | 376/227 |
| 3,812,843 | A * | 5/1974 | Wootten | A61M 5/14546 |
| | | | | 128/DIG. 1 |
| 4,273,122 | A * | 6/1981 | Whitney | A61B 5/0215 |
| | | | | 128/DIG. 1 |
| 4,300,554 | A | 11/1981 | Hessberg et al. | |
| 4,430,079 | A | 2/1984 | Thill et al. | |
| 4,615,269 | A * | 10/1986 | Holder | F42C 15/40 |
| | | | | 102/221 |
| 5,342,823 | A | 8/1994 | Kuhlmeyer et al. | |
| 5,692,693 | A * | 12/1997 | Yamaguchi | A01K 89/01555 |
| | | | | 242/288 |
| 6,065,711 | A * | 5/2000 | Plath | B65H 59/225 |
| | | | | 242/150 M |
| 2007/0000741 | A1 * | 1/2007 | Pribonic | H02K 49/046 |
| | | | | 188/267 |

FOREIGN PATENT DOCUMENTS

| | | |
|---|---|---|
| EP | 0 016 343 A1 | 10/1980 |
| EP | 0 598 678 A1 | 5/1994 |
| WO | WO 2012/120765 A1 | 9/2012 |

* cited by examiner

CONTINUOUS INFUSION DEVICE

PRIORITY

This application is the national stage entry of International Application No. PCT/EP2013/003825 entitled "CONTINUOUS INFUSION DEVICE" filed on 23 Jan. 2015 and published as WO 2014/111114 on 24 Jul. 2014, which claims foreign priority to DE 20 2013 000 4118, filed on 16 Jan. 2013.

The invention relates to a device for continuous infusion for the administration of drugs to treat multiple sclerosis, for example, according to the preamble of claim 1. This continuous infusion device has a housing, in which an infusion apparatus can be inserted, said infusion apparatus comprising at least one infusion liquid container, which can be pressed out. Furthermore, an actuating device for pressing out the infusion apparatus and a drive for moving the actuating device are provided in the continuous infusion device, said drive being supplied with the required drive energy via a mechanical energy storage device. Moreover, the continuous infusion device has a mechanical control arrangement, by means of which a desired speed of the actuating device can be set.

Using such mechanically driven continuous infusion devices, small doses of a drug can be dispensed into the bloodstream of a patient continuously over several hours independent of a local mains power supply or a battery voltage. This facilitates a very flexible and, for example, mobile use of the devices, no precautionary measures whatsoever having to be taken with regard to a possible power cut or insufficient battery voltage during an infusion procedure either.

A device for continuous infusion is known from DE 29 06 830 B1, which device is driven by a mechanical feed mechanism as well as having a purely mechanical feed control. The feed control is formed by a clock mechanism in this case. The feed mechanism and the clock mechanism are each driven by a respective spiral tension spring, both spiral tension springs being tensioned when a housing cover is opened.

A disadvantage of the known mechanical continuous infusion devices is that they have very high production costs in particular because of the clock mechanism used and are relatively sensitive to external influences. Furthermore, the clock mechanism is subject to a certain amount of wear and has to be readjusted at certain time intervals in order to be able to ensure precise functioning.

The object of the invention is to prevent the disadvantages referred to in the case of a generic continuous infusion device and to ensure reliable continuous infusion at low production costs.

This object is achieved by a continuous infusion device having the features of claim 1. In this case, the control arrangement has a brake device having at least one brake element, which can be braked and is motion-coupled to the drive. Furthermore, magnetic means are provided on the brake device, by means of which a magnetic field can be generated that applies a brake force or a brake torque to the brake element. In this way, the brake element can be braked without contact by the brake force or brake torque in order to be able to set a speed or a speed profile of the drive thereby. As a result, a particularly long and maintenance-free service life of the control arrangement is made possible, by means of which arrangement the respective infusion procedures can be performed precisely at the respective set speed.

In a particularly advantageous embodiment, the brake element is formed by a brake disc, which can be rotated by means of the drive. In this case, the brake device can be designed as an eddy current brake or a hysteresis brake, for example. As a result of this, the continuous infusion device can be produced relatively simply and cost-effectively, in particular when using customary eddy current- or hysteresis brake devices.

In this case it is advantageous for the magnetic means to be formed by at least one permanent magnet held at a distance from the brake element, as a result of which the brake device can be produced particularly cost-effectively and operated in a substantially wear-free manner.

Advantageously, the position of the magnetic means for setting the brake force in relation to the brake element is adjustable. As a result of this, the respective required length of infusion can be adjusted particularly simply and precisely by means of the brake device.

Furthermore, it is advantageous for the magnetic means to be adjustable by means of a first adjusting element that can be actuated outside of the housing in order to facilitate a particularly convenient setting of the respective required length of infusion.

Moreover, the control arrangement advantageously has a switchable gear mechanism between the drive and the brake element, which can be switched between at least two different transmissions, as a result of which very different speeds can be set, which in turn allows a particularly variable possible use of the continuous infusion device.

In this case it is advantageous for the gear mechanism to be formed by a switchable planetary gear set, in particular in the form of a Ravigneaux gear set for example, which allows a smooth shift between the different gears.

Furthermore, the gear mechanism is advantageously switchable in this case by means of a second adjusting element that can be actuated outside of the housing. As a result of this, firstly a rough setting of the required infusion time is possible by means of the second adjusting element and, in addition, a fine adjustment is possible by means of the first adjusting element, which in turn allows a particularly variable use of the infusion device on the one hand and on the other hand a particularly accurate setting of the infusion time or the infusion speed.

Moreover, it is advantageous for the actuating device to have a carriage, which is displaceable along a spindle that is rotationally coupled to the brake element, and on which a spindle nut, which meshes with the spindle, as well as an impact element which can be applied to a tappet of the infusion apparatus are provided. As a result of this, a particularly precise transmission of the brake torque acting on the brake element onto the linear movement of the impact element acting on the infusion apparatus is made possible.

In this case, the mechanical energy storage device is advantageously formed by a constant-force spring, which can be tensioned by hand and which acts on the carriage. As a result of this, a particularly even application of pressure on the infusion apparatus is possible throughout the duration of the infusion procedures.

Furthermore, it is advantageous for the infusion apparatus to be retained in an infusion apparatus receptacle, which is displaceable in relation to the actuating device before activation of the actuating device of the infusion liquid container in order to be able to compensate for different filling quantities of the infusion liquid container. This ensures that irrespective of the volume of the drug accommodated in the infusion apparatus, said drug can be administered in the prescribed dose without substantial delay when the infusion procedure commences.

In this case, the housing advantageously has a cover, which can be swivelled between an open position and a closed position, the infusion apparatus receptacle being displaceable by means of a displacement transducer, to which pressure can be applied when the cover is swivelled into the closed position. As a result of this, a volume tolerance adjustment is automatically performed every time the housing is closed such that a precise dose of the drug is ensured over the whole duration of the application irrespective of each volume of the drug received.

Moreover, it is advantageous for a first locking mechanism to be provided, which is adjustable depending on a position of the actuating device between a locked position, in which the cover can be locked in the closed position and a passive position, in which the cover can be swivelled from the closed position into the open position. As a result of this, opening of the housing during an infusion procedure can be reliably prevented.

It is also advantageous here if the actuating device can be activated by a start-up element that can be actuated outside of the housing and a second locking mechanism is provided, which blocks the actuation of the start-up element when the cover is in the open position. In this way, an accidental activation of the infusion device in the open state of the housing in particular when preparing a new infusion procedure can be prevented.

In a further advantageous embodiment of the infusion device, an acoustic signal generator is provided, which can be activated by the actuating device at the end of a displacement movement thereof. As a result of this, the actuating device itself can be used to trigger the signal generator at the end of the displacement movement. As a result of this, the end of the infusion application can be signalled to the patient concerned particularly accurately and reliably.

Moreover, it is advantageous for the signal generator to have a bell as well as an impact element that is lockable in a pre-stressed position and can be displaced against the bell by momentum, it being possible to release the locking by means of the actuating device. As a result of this, a particularly precise and purely mechanical signal generator is provided.

In an alternative embodiment to this, the signal generator is formed by an electronic signal generator, which is connected to an energy storage device that can be charged via a generator. By means of this generator, the drive can be braked at least in part. As a result of this, the brake procedure can be used at least in part to generate energy in order to supply said energy to a cost-effective electronic signal generator.

In this case it is particularly advantageous for the brake device to be formed by the generator, as a result of which the brake device functions as the energy supplier to the signal generator at the same time as its braking function. As a result of this, the construction of the continuous infusion device can be simplified considerably, which in turn allows more cost-effective production.

Figure 2:
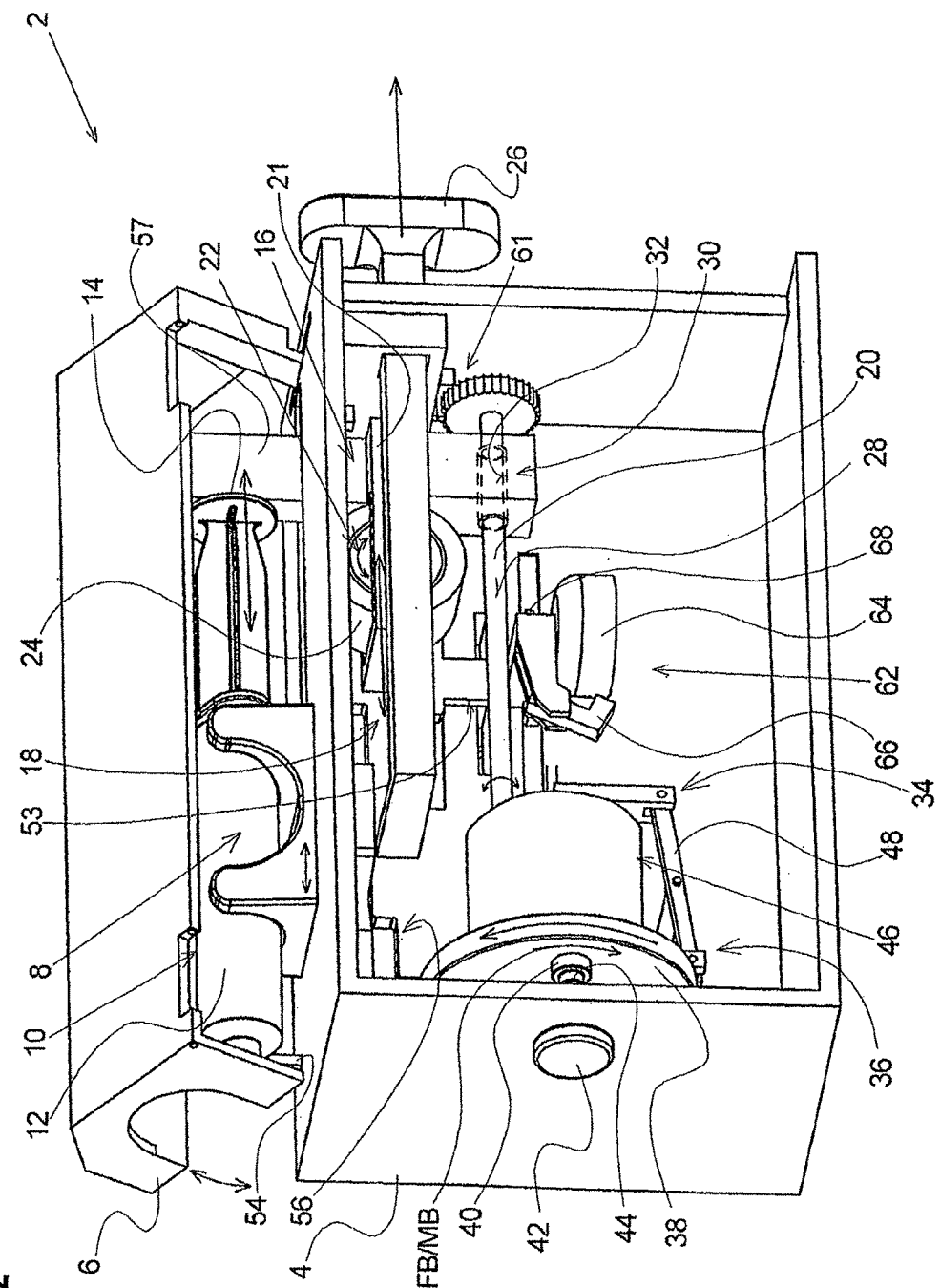
Figure 3:
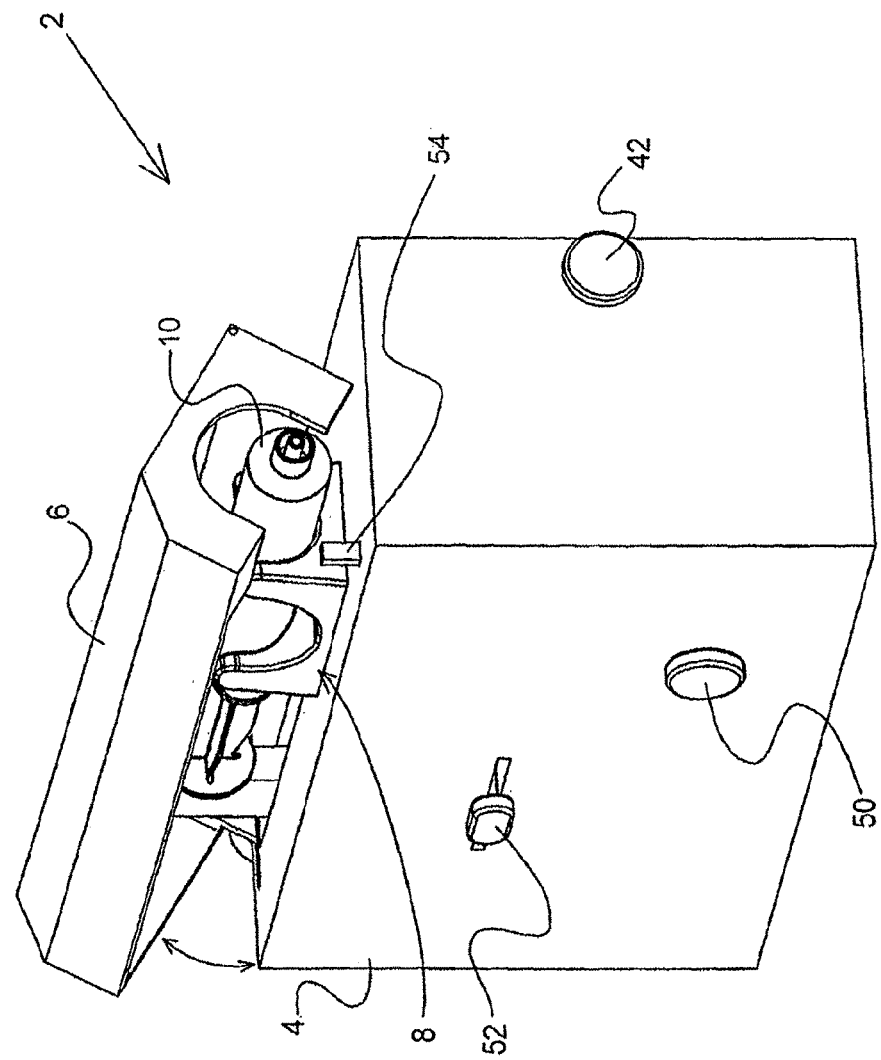

An embodiment of the invention is shown by way of example in the drawings, in which:

FIG. 1 is a view of a back of a continuous infusion device according to the invention with the back housing section removed, FIG. 2 is a perspective view of the back of the continuous infusion device according to FIGS. 1, and FIG. 3 is a view of a front of the continuous infusion device according to FIG. 1.

FIGS. 1 and 2 show a continuous infusion device 2 comprising a housing 4 on which an infusion apparatus receptacle 8 is accommodated in an upper region, which can be closed by a cover 6. An injection-shaped infusion apparatus 10 can be inserted into said infusion apparatus receptacle 8, said infusion apparatus having an infusion liquid container 12 in which a medium M, constituted by a drug for treating multiple sclerosis, for example, can be accommodated and can be pressed out by applying pressure to a tappet 14 of the infusion apparatus 10.

In order to apply pressure to the tappet 14, an actuating device 16 is provided here, which can be displaced along a spindle 20 by means of a drive 18. In this case, the actuating device 16 has a carriage 21, which can be moved along the spindle 20 and on which a mechanical energy storage device 22 acts. This energy storage device 22 has a windable constant-force spring 24, for example, which can be drawn back by means of a tension element 26 that is easy to handle from outside of the housing 4.

The spindle 20 here forms an external thread 28, which interacts with an internal thread 30 of a spindle nut 32 that is integrated into the actuating device 16. Moreover, the spindle 20 is coupled to a control arrangement 34, by means of which a user of the continuous infusion device 2 can set a desired infusion speed or infusion time.

The control arrangement 34 has a brake device 36 for adjusting the desired infusion speed. Said brake device provides a brake element 38 in the form of a brake disc, which can be set into rotary motion by means of the drive 18. In the process, the brake element 38 interacts with magnetic means 40, which are kept at a distance and which are formed by a permanent magnet, for example, and generate a magnetic field, which generates a brake force FB or a brake torque MB on the brake element 38 in the manner of a eddy current brake. In this case, the strength of the brake force FB or brake torque MB depends on the position of the magnetic means 40 in relation to the brake element 38, which means can be adjusted using a first adjusting element 42, which can be actuated from outside of the housing 4 and is coupled to the magnetic means 40 via a first gear rod linkage 44.

Moreover, the control arrangement 34 has a gear mechanism 46 to set the desired infusion speed, which comprises a planetary gear set, for example, which can be switched between at least two transmissions, in the form of a Ravigneaux gear set. In this case, a second gear rod linkage 48 is provided to switch the gear mechanism 46, which linkage can be shifted from outside of the housing 4 using a second adjusting element 50, as can be seen from FIG. 3.

Moreover, a third adjusting element 52, via which the patient can set the required infusion quantity of the medium M, is provided on the housing 4. The position of an impact element 53, which serves as an end stop for the actuating device 16, can be adjusted here using the adjusting element 52.

As can also be seen from FIG. 3, a displacement transducer 54 is provided on the housing 4, to which transducer pressure is applied by the cover 6 when said cover is swivelled from the open position shown into a closed position. In this case, the displacement transducer 54 is part of a tolerance compensation mechanism 56, by means of which the infusion apparatus receptacle 8 can be displaced in relation to the actuating device 16 until the tappet 14 of the infusion apparatus 10 abuts an impact element 57 of the actuating device 16 without clearance, irrespective of the actual filling quantity of the medium M.

As can be seen from FIG. 1, a locking device 58 is also provided in the housing 4, said locking device having a first locking mechanism, which can be switched between a locked position and a passive position depending on the respective current position of the actuating device 16. In this case, the first locking mechanism prevents the cover 6 from swivelling into the open position as long as the actuating device 16 is not in an initial position, which corresponds, for example, to its position when the energy storage device 22 is fully tensioned.

In addition, the locking device 58 has a second locking mechanism, which blocks a start-up of the continuous infusion device 2 via a start-up element 60 according to FIG. 1, which is in the form of a push button, for example, as long as the cover 6 is not in the closed position. In this blocked position, the start-up element 60 prevents the drive 18 from being able to be accidentally activated by means of a locking device 61 connected to the spindle 20.

Any known and suitable device, such as a device which has an adjustable retaining pawl and a corresponding pawl receptacle, can be used here as the first and second locking mechanism.

As can also be seen from FIGS. 1 and 2, an acoustic signal generator 62 is also provided, which has a bell 64 and an impact element 66. In this case, the impact element 66 is secured at a distance from the bell 64 in the shown tensioned initial position of the energy storage device 22, for example by means of a customary releasable pawl device and pre-stressed towards the bell 64 by a spring device (not shown). The securing of the impact element 66 in this pre-stressed position can be reversed in this case by a release element 68, to which pressure can be applied by means of the actuating device 16. In this case, the release element 68 is arranged substantially at the height of the end stop that serves to set the infusion quantity to be administered and is retained on the impact element 53, for example, for this purpose.

As an alternative to the mechanical signal generator 62, it would also be possible to use an electronic signal generator (not shown). Said signal generator could be operated, for example, by means of an energy storage device, which is charged by a generator. Such a generator could also simultaneously function as part of the brake device 36 or be driven directly by the gear mechanism 46 or the spindle 20 and thus likewise act on the drive 18 with a preferably adjustable brake torque MB.

In the process, the functioning of the continuous infusion device is as follows in any case:

To prepare for a new infusion procedure, after the infusion performed most recently the energy storage device 22 of the drive 18 must first be re-tensioned by pulling the tension element 26, the actuating device 16 also being brought into the initial position shown.

In this initial position the first locking mechanism of the locking device 58 is brought into the passive position, such that the patient can move the cover 6 from the closed position into the shown open position in order to be able to insert a new infusion apparatus 10 containing the medium M into the infusion apparatus receptacle 8.

Then the patient can swivel the cover 6 back into the closed position, said cover applying pressure to the displacement transducer 54 such that the infusion apparatus receptacle 8 is displaced until the tappet 14 of the accommodated infusion apparatus 10 abuts the impact element 57 of the actuating device 16. At the same time, as a result of the swivelling of the cover 6 into the closed position, the second locking mechanism of the locking device 58 is moved from its blocked position into a passive position in which the start-up element 60 can be actuated.

Now the patient can set a desired infusion speed by means of the first and second adjusting element 42, 50, the second adjusting element 50 serving, for example, to set a rough speed gradation, the switch positions of which can be indicated for example by descriptions such as "fast", "medium" and "slow". In addition, the first adjusting element 42 serves to make a fine adjustment of the infusion speed by positioning the magnetic means 40.

Moreover, the patient can set the position of the end stop for the actuating device 16 and thus the volume of the medium M to be administered by means of the third adjusting element 52.

After this, the continuous infusion device 2 is set and ready for operation for the intended application.

When pressure is applied to the start-up element 60, said element releases the locking device 61 on the spindle 20, such that said spindle is in set into rotation by the restoring force of the constant-force spring 24 that acts on the actuating device 16 and the interaction of the internal thread 30 of the spindle nut 32 with the external thread 28 of the spindle 20. In this case, the impact element 57 of the actuating device 16 is pressed against the tappet 14 of the infusion apparatus 10 and the medium M is thus pressed out of the infusion liquid container 12, said medium being supplied to a patient by means of a tube and a needle (not shown), for example.

As a result of the motion-coupling of the spindle 20 to the brake device 36, the brake torque MB generated here by means of the magnetic means 40 and the brake element 38 also acts on the spindle 20 and via the spindle on the actuating device 16. In this way, said actuating device only moves during the infusion procedure at the speed set on the first and second adjusting element or over the corresponding infusion time.

In the process, the cover 6 is prevented from opening during the current infusion procedure by the first locking mechanism of the locking device 58, said first locking mechanism being in the locked position. Furthermore, during the current infusion procedure, apart from the start-up element 60, which can be moved into an off position of the continuous infusion device 2 if need be, all other adjusting elements are also locked in the set position in order to prevent an accidental adjustment during the infusion procedure.

Normally, the infusion procedure is ended by the actuating device 16 impacting on the end stop positioned by the third adjusting element 52, as a result of which the actuating device 16 cannot be displaced any further by the constant-force spring 24. Substantially simultaneously, the actuating device also applies pressure to the release element 68, which releases the impact element 66 in the process which in turn is accelerated by momentum against the bell 64.

The patient is informed by the sounding of the bell 64 that the infusion procedure is finished.

The invention claimed is:

1. Device for continuous infusion comprising a housing, in which an infusion apparatus can be inserted, said infusion apparatus comprising at least one infusion liquid container, which can be pressed out,
   an actuating device for pressing out the infusion apparatus,
   a drive for moving the actuating device, said drive having a mechanical energy storage device, and
   a mechanical control arrangement, by means of which a speed of the actuating device can be set, wherein the control arrangement has a brake device that provides at least one brake element which can be braked and is motion-coupled to the drive, and magnetic means, by means of which a magnetic field can be generated that applies a brake force to the brake element, and wherein the position of the magnetic means can be adjusted in order to set the brake force in relation to the brake element.

2. Continuous infusion device according to claim 1, wherein the brake element is formed by brake disc, which can be rotated by means of the drive.

3. Continuous infusion device according to claim 2, wherein the magnetic means are formed by at least one permanent magnet held at a distance from the brake element.

4. Continuous infusion device according to claim 1, wherein the magnetic means are formed by at least one permanent magnet held at a distance from the brake element.

5. Continuous infusion device according to claim 1, wherein the magnetic means can be adjusted using a first adjusting element that can be actuated outside of the housing.

6. Continuous infusion device according to claim 1, wherein the control arrangement also has a gear mechanism between the drive and the brake element that can be switched between at least two different transmissions.

7. Continuous infusion device according to claim 6, wherein the gear mechanism is formed by a switchable planetary gear set.

8. Continuous infusion device according to claim 6, wherein the gear mechanism can be switched by means of a second adjusting element that can be actuated outside of the housing.

9. Continuous infusion device according to claim 1, wherein the actuating device has a carriage, which can be moved along a spindle that is rotationally coupled to the brake element and on which a spindle nut that meshes with the spindle and an impact element, which can be placed against a tappet of the infusion apparatus, are provided.

10. Continuous infusion device according to claim 9, wherein the mechanical energy storage device is formed by a constant-force spring, which can be tensioned by hand and acts on the carriage.

11. Continuous infusion device according to claim 1, wherein the infusion apparatus is retainable in an infusion apparatus receptacle, which can be moved in relation to the actuating device before activation of the actuating device in order to compensate for different filling quantities of the infusion liquid container.

12. Continuous infusion device according to claim 11, wherein the housing has a cover, which can be swivelled between an open position and a closed position, and the infusion apparatus receptacle can be moved by means of a displacement transducer to which pressure can be applied when the cover is swivelled into the closed position.

13. Continuous infusion device according to claim 12, wherein the actuating device can be activated by a start-up element that can be actuated from outside of the housing and a second locking mechanism is provided, which blocks the actuation of the start-up element when the cover is in the open position.

14. Continuous infusion device according to claim 11, wherein a first locking mechanism is provided, which can be adjusted between a locked position, in which the cover can be locked in the closed position and a passive position, in which the cover can be swivelled from the closed position into the open position depending on a position of the actuating device.

15. Continuous infusion device according to claim 1, wherein an acoustic signal generator is provided which can be activated by the actuating device at the end of a displacement movement thereof.

16. Continuous infusion device according to claim 15, wherein the signal generator has a bell and an impact element (66) that is lockable in a pre-stressed position and can be moved against the bell by momentum, it being possible to release the locking by means of the actuating device.

17. Continuous infusion device according to claim 15, wherein the signal generator is formed by an electronic signal generator, which is connected to an energy storage device that can be charged by a generator and by means of which the drive can be braked at least in part.

18. Continuous infusion device according to claim 17, wherein the brake device is formed by the generator.

* * * * *